United States Patent
Tanisaka et al.

(10) Patent No.: US 10,772,895 B2
(45) Date of Patent: Sep. 15, 2020

(54) PHARMACEUTICAL COMPOSITION

(71) Applicant: FUJIFILM CORPORATION, Minato-ku, Tokyo (JP)

(72) Inventors: Hiroki Tanisaka, Kanagawa (JP); Kyoko Senga, Kanagawa (JP); Shuhei Osaka, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/137,493

(22) Filed: Sep. 20, 2018

(65) Prior Publication Data

US 2019/0022108 A1 Jan. 24, 2019

Related U.S. Application Data

(63) Continuation of application No. PCT/JP2017/014297, filed on Apr. 5, 2017.

(30) Foreign Application Priority Data

| Apr. 6, 2016 | (JP) | 2016-076759 |
| Oct. 17, 2016 | (JP) | 2016-203705 |
| Mar. 28, 2017 | (JP) | 2017-063914 |

(51) Int. Cl.
| A61K 31/565 | (2006.01) |
| A61K 9/08 | (2006.01) |
| A61K 47/10 | (2017.01) |
| A61K 47/44 | (2017.01) |
| A61K 9/00 | (2006.01) |

(52) U.S. Cl.
CPC .......... *A61K 31/565* (2013.01); *A61K 9/0019* (2013.01); *A61K 9/08* (2013.01); *A61K 47/10* (2013.01); *A61K 47/44* (2013.01)

(58) Field of Classification Search
CPC ...... A61K 31/565; A61K 9/0019; A61K 9/08; A61K 47/44; A61K 47/10
See application file for complete search history.

(56) References Cited

U.S. PATENT DOCUMENTS

| 2001/0020016 A1 | 9/2001 | Evans et al. | |
| 2016/0213682 A1* | 7/2016 | Ahmed | A61K 9/0019 |
| 2017/0027958 A1* | 2/2017 | Patel | A61K 31/565 |

FOREIGN PATENT DOCUMENTS

| CN | 103070871 A | 5/2013 |
| CN | 104224702 A | 12/2014 |
| JP | 2004-107353 A | 4/2004 |
| JP | 2004-534093 A | 11/2004 |
| JP | 3713237 B2 | 11/2005 |
| JP | 2009-509942 A | 3/2009 |
| WO | 1997/021440 A1 | 6/1997 |
| WO | 2003/006064 A1 | 11/2004 |
| WO | 2007/033434 A1 | 3/2007 |
| WO | 2015/033302 A2 | 3/2015 |

OTHER PUBLICATIONS

International Search Report issued in International Application No. PCT/JP2017/014297 dated Jun. 27, 2017.
Written Opinion of the ISA issued in International Application No. PCT/JP2017/014297 dated Jun. 27, 2017.
English language translation of the following: Office action dated Jul. 30, 2019 from the JPO in a Japanese patent application No. 2018-510648 corresponding to the instant patent application.
Extended European Search Report dated Mar. 20, 2019, issued in corresponding EP Patent Application No. 17779188.6.
English language translation of the following: Office action dated Nov. 12, 2019 from the JPO in a Japanese patent application No. 2018-510648 corresponding to the instant patent application.
English language translation of the following: Office action dated Feb. 6, 2020 from the SIPO in a Chinese patent application No. 201780020249.0 corresponding to the instant patent application. This office action translation is submitted now in order to supplement the understanding of the cited reference which is being disclosed in the instant Information Disclosure Statement.
English language translation of the following: Office action dated Jun. 11, 2020 from the SIPO in a Chinese patent application No. 201780020249.0 corresponding to the instant patent application.

\* cited by examiner

*Primary Examiner* — Sarah Pihonak
*Assistant Examiner* — Jason Deck
(74) *Attorney, Agent, or Firm* — Solaris Intellectual Property Group, PLLC

(57) ABSTRACT

Provided is a pharmaceutical composition which contains fulvestrant in an amount of equal to or greater than 8% by mass with respect to the entire mass of the pharmaceutical composition, an aqueous solvent satisfying (1) to (4), and a pharmaceutically acceptable nonaqueous carrier satisfying (A) and (B). (1) Ethanol is contained in an amount of equal to or greater than 8% by mass with respect to the entire mass of the pharmaceutical composition. (2) At least one kind of polyhydric alcohol selected from propylene glycol or 1,3-butylene glycol is contained in an amount of equal to or greater than 3% by mass with respect to the entire mass of the pharmaceutical composition. (3) A content of benzyl alcohol is less than 5% by mass with respect to the entire mass of the pharmaceutical composition. (4) A content of the aqueous solvent is 15% to 50% by mass with respect to the entire mass of the pharmaceutical composition. (A) A content of benzyl benzoate is less than 1% by mass with respect to the entire mass of the pharmaceutical composition. (B) A content of the nonaqueous carrier is 40% to 75% by mass with respect to the entire mass of the pharmaceutical composition.

9 Claims, No Drawings

PHARMACEUTICAL COMPOSITION

CROSS-REFERENCE TO RELATED APPLICATIONS

This application is a continuation application of International Application No. PCT/JP2017/014297, filed Apr. 5, 2017, the disclosure of which is incorporated herein by reference in its entirety. Further, this application claims priority from Japanese Patent Application No. 2016-076759, filed Apr. 6, 2016, Japanese Patent Application No. 2016-203705, filed Oct. 17, 2016, and Japanese Patent Application No. 2017-063914, filed Mar. 28, 2017, the disclosures of which are incorporated herein by reference in their entirety.

BACKGROUND OF THE INVENTION

1. Field of the Invention

The present invention relates to a pharmaceutical composition.

2. Description of the Related Art

Fulvestrant (7α-[9-(4,4,5,5,5-pentafluoropentylsulfinyl) nonyl]estra-1,3,5(10)-triene-3,17β-diol) is an estrogen receptor antagonist and is marketed under a trade name of FASLODEX (registered trademark) as an intramuscular injection preparation by AstraZeneca. FASLODEX is supplied in the form of a 5 mL previously-filled syringe that contains fulvestrant at an indicated amount of 50 mg/mL and contains, as additives, ethanol, benzyl alcohol, benzyl benzoate, and castor oil.

In clinical practice, two syringes, that is, a 10 mL preparation in total (500 mg as fulvestrant) is applied as a single dose.

In recent years, various reports on pharmaceutical preparations containing fulvestrant have been made.

For example, JP3713237B and JP2004-534093A disclose pharmaceutical preparations suitable for intramuscular injection which contain fulvestrant, pharmaceutically acceptable alcohols (ethanol, benzyl alcohol, and the like), benzyl benzoate, and castor oil.

JP2009-509942A discloses a preparation that contains fulvestrant, pharmaceutically acceptable alcohol (ethanol, benzyl alcohol, and the like), propylene glycol or polyethylene glycol, and castor oil.

SUMMARY OF THE INVENTION

As described above, due to necessity of injecting a 5 mL liquid at two locations, intramuscular injection preparations containing fulvestrant in the related art place a heavy burden on patients. In a case where the number of injection sites is reduced to one location or a dose per injection site is reduced for the purpose of reducing the burden on patients, it is necessary to contain fulvestrant at a higher concentration in a pharmaceutical preparation.

However, in a case where a pharmaceutical preparation containing fulvestrant at a high concentration is intramuscularly injected, a problem that fulvestrant is precipitated at an injection site and a precipitated particulate fulvestrant causes tissue irritation (that is, pain) or inflammation can occur.

In connection with the above-described matters, JP3713237B realizes a pharmaceutical preparation containing fulvestrant in an amount of equal to or greater than 45 mg/mL by adjusting blending amounts of alcohols, benzyl benzoate, and castor oil. However, it is described that in a case where the pharmaceutical preparation described in JP3713237B is intramuscularly injected, a significant tissue irritation or inflammation at an injection site can be caused due to presence of particulate fulvestrant.

In JP2004-534093A, a pharmaceutical preparation containing fulvestrant in an amount of equal to or greater than 100 mg/mL is realized by increasing blending amounts of alcohols and benzyl benzoate, as compared with the pharmaceutical preparation described in JP3713237B. However, JP2004-534093A describes that in a case where the pharmaceutical preparation described in JP2004-534093A is intramuscularly injected, sedimentation occurs at an injection site, and causes a tissue irritation or inflammation stronger than that of the pharmaceutical preparation described in JP3713237B.

As a result of checking the preparation described in JP2009-509942A, the present inventors found that the preparation can contain fulvestrant in an amount of equal to or greater than 10% by mass (that is, 100 mg/mL) with respect to the entire mass of the preparation. However, with respect to the preparation described in JP2009-509942A, the present inventors conducted an evaluation test (evaluation test for precipitation properties described in Examples as described later) assuming an environment after intramuscular injection. As a result, precipitation of fulvestrant was identified.

That is, even though a pharmaceutical preparation can contain fulvestrant at a high concentration, it is still a problem to be solved that fulvestrant can be precipitated in a case of being brought into contact with a body fluid after intramuscular injection.

One embodiment of the present invention has been made in view of the circumstances as described above, and an object of the present invention is to provide a pharmaceutical composition which contains fulvestrant at a concentration which is high as compared with the related art and in which precipitation of fulvestrant becomes difficult to occur even in a case of being brought into contact with a body fluid.

Specific means for achieving the above-mentioned object includes the following embodiments.

[1] A pharmaceutical composition comprising:
fulvestrant;
an aqueous solvent; and
a pharmaceutically acceptable nonaqueous carrier,
in which a content of the fulvestrant is equal to or greater than 8% by mass with respect to the entire mass of the pharmaceutical composition, the aqueous solvent satisfies the following requirements (1) to (4), and the pharmaceutically acceptable nonaqueous carrier satisfies the following requirements (A) and (B).

(1) ethanol is contained in an amount of equal to or greater than 8% by mass with respect to the entire mass of the pharmaceutical composition (2) at least one kind of polyhydric alcohol selected from propylene glycol or 1,3-butylene glycol is contained in an amount of equal to or greater than 3% by mass with respect to the entire mass of the pharmaceutical composition (3) a content of benzyl alcohol is less than 5% by mass with respect to the entire mass of the pharmaceutical composition (4) a content of the aqueous solvent is 15% by mass to 50% by mass with respect to the entire mass of the pharmaceutical composition (A) a content of benzyl benzoate is less than 1% by mass with respect to the entire mass of the pharmaceutical composition (B) a content of the pharmaceutically acceptable nonaqueous carrier is 40% by mass to 75% by mass with respect to the entire mass of the pharmaceutical composition

[2] The pharmaceutical composition according to [1], in which the content of the fulvestrant is 8% by mass to 14% by mass with respect to the entire mass of the pharmaceutical composition.

[3] The pharmaceutical composition according to [1] or [2], in which the at least one kind of polyhydric alcohol selected from propylene glycol or 1,3-butylene glycol is propylene glycol.

[4] The pharmaceutical composition according to any one of [1] to [3], in which the pharmaceutically acceptable nonaqueous carrier is castor oil, or a mixture of castor oil and vegetable oil which is different from castor oil.

[5] The pharmaceutical composition according to [4], in which the vegetable oil which is different from castor oil is at least one kind of vegetable oil selected from the group consisting of sesame oil, peanut oil, soybean oil, camellia oil, corn oil, cottonseed oil, olive oil, safflower oil, rapeseed oil, and a fatty acid triglyceride of which constituent fatty acids have 6 to 12 carbon atoms on average.

[6] The pharmaceutical composition according to [4], in which the vegetable oil which is different from castor oil is at least one kind of vegetable oil selected from sesame oil or peanut oil.

[7] The pharmaceutical composition according to any one of [1] to [6], in which the pharmaceutically acceptable nonaqueous carrier further satisfies the following requirements (C) and (D).

(C) castor oil is contained in an amount of equal to or greater than 40% by mass with respect to the entire mass of the pharmaceutical composition (D) a content of the vegetable oil which is different from castor oil is less than 20% by mass with respect to the entire mass of the pharmaceutical composition

[8] The pharmaceutical composition according to any one of [1] to [7], in which a content of ethanol is 10% by mass to 20% by mass with respect to the entire mass of the pharmaceutical composition.

[9] The pharmaceutical composition according to any one of [1] to [8], in which a content of the at least one kind of polyhydric alcohol selected from propylene glycol or 1,3-butylene glycol is 10% by mass to 20% by mass with respect to the entire mass of the pharmaceutical composition.

[10] A pharmaceutical composition comprising:
fulvestrant;
an aqueous solvent; and
a pharmaceutically acceptable nonaqueous carrier,
in which a content of the fulvestrant is equal to or greater than 8% by mass with respect to the entire mass of the pharmaceutical composition, the aqueous solvent satisfies the following requirements (i) to (iv), and the pharmaceutically acceptable nonaqueous carrier satisfies the following requirements (a) to (d).

(i) ethanol is contained in an amount of 10% by mass to 20% by mass with respect to the entire mass of the pharmaceutical composition (ii) propylene glycol is contained in an amount of 10% by mass to 20% by mass with respect to the entire mass of the pharmaceutical composition (iii) a content of benzyl alcohol is less than 5% by mass with respect to the entire mass of the pharmaceutical composition (iv) a content of the aqueous solvent is 20% by mass to 40% by mass with respect to the entire mass of the pharmaceutical composition (a) a content of benzyl benzoate is less than 1% by mass with respect to the entire mass of the pharmaceutical composition (b) castor oil is contained in an amount of equal to or greater than 40% by mass with respect to the entire mass of the pharmaceutical composition (c) a content of at least one kind of vegetable oil selected from sesame oil or peanut oil is less than 20% by mass with respect to the entire mass of the pharmaceutical composition (d) a content of the pharmaceutically acceptable nonaqueous carrier is 40% by mass to 75% by mass with respect to the entire mass of the pharmaceutical composition

[11] The pharmaceutical composition according to any one of [1] to [10], in which the content of benzyl alcohol is equal to or less than 2% by mass with respect to the entire mass of the pharmaceutical composition.

[12] The pharmaceutical composition according to any one of [1] to [11], which is for intramuscular injection.

According to one embodiment of the present invention, there is provided a pharmaceutical composition which contains fulvestrant at a concentration which is high as compared with the related art and in which precipitation of fulvestrant becomes difficult to occur even in a case of being brought into contact with a body fluid.

DESCRIPTION OF THE PREFERRED EMBODIMENTS

Hereinafter, an example of an embodiment of a pharmaceutical composition to which the present invention is applied will be described. However, the present invention is not limited to the following embodiment at all, and it is possible to practice the present invention with appropriate modifications within a scope of a purpose of one embodiment of the present invention.

In the present specification, a numerical range expressed using "to" means a range including numerical values described before and after the preposition "to" as a minimum value and a maximum value, respectively.

In numerical ranges described in a stepwise manner in the present specification, an upper limit value or a lower limit value described in a certain numerical range may be replaced with an upper limit value or a lower limit value of another numerical range described in a stepwise manner. In addition, in numerical ranges described in the present disclosure, an upper limit value or a lower limit value described in a certain numerical range may be replaced with values shown in Examples.

In the present specification, in a case where a plurality of substances corresponding to each ingredient is present in a pharmaceutical composition, unless otherwise specified, an amount of each ingredient in the pharmaceutical composition means a total amount of the plurality of substances present in the pharmaceutical composition.

In the present specification, the term "step" not only includes an independent step, but also steps in a case where an intended purpose of the step is achieved even though it is not possible to make a clear distinction from the other step.

In the present specification, "low temperature" generally refers to a temperature applied in a case where a pharmaceutical composition containing fulvestrant as an active ingredient is refrigerated and stored, and specifically means a range of 2° C. to 8° C.

[Pharmaceutical Composition]

A pharmaceutical composition of the present embodiment contains fulvestrant, an aqueous solvent, and a pharmaceutically acceptable nonaqueous carrier (hereinafter also simply referred to as "nonaqueous carrier"), in which a content of fulvestrant is equal to or greater than 8% by mass with respect to the entire mass of the pharmaceutical composition, the aqueous solvent satisfies the following requirements (1) to (4), and the pharmaceutically acceptable nonaqueous carrier satisfies the following requirements (A) and (B).

(1) Ethanol is contained in an amount of equal to or greater than 8% by mass with respect to the entire mass of the pharmaceutical composition. (2) At least one kind of polyhydric alcohol (hereinafter also referred to as "specific polyhydric alcohol") selected from propylene glycol or 1,3-butylene glycol is contained in an amount of equal to or greater than 3% by mass with respect to the entire mass of the pharmaceutical composition. (3) A content of benzyl alcohol is less than 5% by mass with respect to the entire mass of the pharmaceutical composition. (4) A content of the aqueous solvent is 15% by mass to 50% by mass with respect to the entire mass of the pharmaceutical composition.

(A) A content of benzyl benzoate is less than 1% by mass with respect to the entire mass of the pharmaceutical composition. (B) A content of the pharmaceutically acceptable nonaqueous carrier is 40% by mass to 75% by mass with respect to the entire mass of the pharmaceutical composition.

Intramuscular injection preparations containing fulvestrant in the related art have a large amount of liquid to be administered and also require to be injected at two sites. Thus, it can be said that a heavy burden is placed on patients. For the purpose of reducing the burden on patients, for example, it is conceivable to reduce injection sites to one location by causing fulvestrant to be contained at a higher concentration in a pharmaceutical preparation, or to reduce a dose per injection site. However, in a case where a pharmaceutical preparation containing fulvestrant at a high concentration is intramuscularly injected, fulvestrant may be precipitated at an injection site. Such a precipitation of fulvestrant can be caused by the fact that after the intramuscular injection, the pharmaceutical preparation is brought into contact with a body fluid and the aqueous solvent that has contributed to improvement of dissolution properties of fulvestrant in the pharmaceutical preparation diffuses into the body fluid. It is considered that at the injection site, fulvestrant which exceeds solubility due to diffusion of the aqueous solvent into the body fluid cannot maintain a dissolved state and is precipitated. A precipitated particulate fulvestrant can cause tissue irritation or inflammation, which is not preferable.

In pharmaceutical preparations containing fulvestrant which have been reported so far, even though it is possible to contain fulvestrant at a high concentration in the pharmaceutical preparation, a problem that in a case where fulvestrant is brought into contact with a body fluid after intramuscular injection, fulvestrant can be precipitated cannot be solved yet.

By containing fulvestrant, an aqueous solvent satisfying the above requirements (1) to (4), and a nonaqueous carrier satisfying the above requirements (A) and (B), the pharmaceutical composition of the present embodiment can exert an effect that precipitation of fulvestrant becomes difficult to occur in a case of being brought into contact with a body fluid while also containing fulvestrant in an amount of equal to or greater than 8% by mass with respect to the entire mass of the pharmaceutical composition.

Hereinafter, the respective ingredients of the pharmaceutical composition of the present embodiment will be described in detail.

<Fulvestrant>

The pharmaceutical composition of the present embodiment contains fulvestrant as an active ingredient.

Fulvestrant (7α-[9-(4,4,5,5,5-pentafluoropentylsulfinyl)nonyl]estra-1,3,5(10)-triene-3,17β-diol) is an estrogen receptor antagonist and is known as a drug for treating breast cancer.

A content of fulvestrant in the pharmaceutical composition of the present embodiment is equal to or greater than 8% by mass, preferably equal to or greater than 9% by mass, and more preferably equal to or greater than 9.5% by mass, with respect to the entire mass of the pharmaceutical composition.

An upper limit is not particularly limited, and is, for example, equal to or less than 30% by mass, preferably equal to or less than 20% by mass, more preferably equal to or less than 14% by mass, and even more preferably equal to or less than 12% by mass.

In a case where the content of fulvestrant in the pharmaceutical composition of the present embodiment is equal to or greater than 8% by mass with respect to the entire mass of the pharmaceutical composition, it is possible to reduce injection sites from two locations in the related art to one location, or to reduce a dose per injection site, which makes it possible to reduce a burden on patients.

<Aqueous Solvent>

The pharmaceutical composition of the present embodiment contains an aqueous solvent in an amount of 15% by mass to 50% by mass with respect to the entire mass of the pharmaceutical composition.

In addition, the aqueous solvent contained in the pharmaceutical composition of the present embodiment contains ethanol in an amount of equal to or greater than 8% by mass with respect to the entire mass of the pharmaceutical composition, and at least one kind of polyhydric alcohol (specific polyhydric alcohol) selected from propylene glycol or 1,3-butylene glycol in an amount of equal to or greater than 3% by mass with respect to the entire mass of the pharmaceutical composition, in which a content of benzyl alcohol in the alcohol is less than 5% by mass with respect to the entire mass of the pharmaceutical composition.

In the present embodiment, the "aqueous solvent" means a solvent having high compatibility with water, specifically, a solvent having a solubility in water at 25° C. of equal to or greater than 1% by mass.

Examples of the aqueous solvent in the present embodiment include ethanol, glycerin, propylene glycol, 1,3-butylene glycol, dipropylene glycol, and benzyl alcohol.

The pharmaceutical composition of the present embodiment contains ethanol in an amount of equal to or greater than 8% by mass with respect to the entire mass of the pharmaceutical composition.

In the pharmaceutical composition of the present embodiment, ethanol contributes to improvement of dissolution properties of fulvestrant in the pharmaceutical composition.

In a case where the content of ethanol in the pharmaceutical composition of the present embodiment is equal to or greater than 8% by mass with respect to the entire mass of the pharmaceutical composition, good dissolution properties of fulvestrant are exhibited, and a pharmaceutical composition which contains fulvestrant at a high concentration, that is, at a concentration of equal to or greater than 8% by mass with respect to the entire mass of the pharmaceutical composition can be realized. In addition, there is a tendency that turbidity becomes difficult to occur in a case of being stored at a low temperature.

The content of ethanol in the pharmaceutical composition of the present embodiment is preferably 10% by mass to 30% by mass, and more preferably 10% by mass to 20% by mass, with respect to the entire mass of the pharmaceutical composition.

Ethanol is not particularly limited as long as a quality that satisfies criteria of Pharmacopoeia (Japan, the United States, Europe, and pharmacopoeias of other countries) is possessed.

As the ethanol in the pharmaceutical composition of the present embodiment, for example, ethanol (one containing 95.1% by volume to 96.9% by volume of ethanol at 15° C.) described in the Japanese Pharmacopoeia and anhydrous ethanol (one containing ethanol in an amount of equal to or greater than 99.5% by volume at 15° C.) are mentioned.

The pharmaceutical composition of the present embodiment contains at least one kind of polyhydric alcohol (specific polyhydric alcohol) selected from propylene glycol or 1,3-butylene glycol in an amount of equal to or greater than 3% by mass with respect to the entire mass of the pharmaceutical composition.

In the pharmaceutical composition of the present embodiment, the specific polyhydric alcohol contributes to improvement of dissolution properties of fulvestrant in the pharmaceutical composition.

In a case where a content of the specific polyhydric alcohol in the pharmaceutical composition of the present embodiment is equal to or greater than 3% by mass with respect to the entire mass of the pharmaceutical composition, good dissolution properties of fulvestrant are exhibited, and a pharmaceutical composition which contains fulvestrant at a high concentration, that is, at a concentration of equal to or greater than 8% by mass with respect to the entire mass of the pharmaceutical composition can be realized.

A content of the specific polyhydric alcohol in the pharmaceutical composition of the present embodiment is preferably 5% by mass to 25% by mass, and more preferably 10% by mass to 20% by mass, with respect to the entire mass of the pharmaceutical composition.

The pharmaceutical composition of the present embodiment may contain, as the specific polyhydric alcohol, only propylene glycol, only 1,3-butylene glycol, or both of propylene glycol and 1,3-butylene glycol.

From the viewpoint of further increasing dissolution properties of fulvestrant, the pharmaceutical composition of the present embodiment preferably contains at least propylene glycol as the specific polyhydric alcohol, and it is particularly preferable that the specific polyhydric alcohol is propylene glycol.

In the pharmaceutical composition of the present embodiment, a content of benzyl alcohol is less than 5% by mass with respect to the entire mass of the pharmaceutical composition.

In a case where the content of benzyl alcohol in the pharmaceutical composition of the present embodiment is less than 5% by mass with respect to the entire mass of the pharmaceutical composition, even though the pharmaceutical composition contains fulvestrant at a high concentration, that is, at a concentration of equal to or greater than 8% by mass with respect to the entire mass of the pharmaceutical composition, there is a tendency that precipitation of fulvestrant becomes difficult to occur in a case of being brought into contact with a body fluid after intramuscular injection.

A content of benzyl alcohol in the pharmaceutical composition of the present embodiment is preferably less than 3% by mass, more preferably equal to or less than 2% by mass, and even more preferably equal to or less than 1% by mass, with respect to the entire mass of the pharmaceutical composition, and particularly preferably benzyl alcohol is not contained, that is, 0% by mass.

In the pharmaceutical composition of the present embodiment, it is preferable that water is not intentionally blended from the viewpoint of suppressing turbidity that may occur in a case of being stored at a low temperature.

As used herein, the phrase "water is not intentionally blended" means that water is not actively blended except water which is inevitably contained due to moisture which is contained at a stage of raw materials of the respective ingredients contained in the pharmaceutical composition of the present embodiment and is brought by the respective ingredients, and water which is inevitably contained due to moisture absorption from the atmosphere. "Water which is inevitably contained due to moisture absorption from the atmosphere" includes water which is retained in the pharmaceutical composition during storage of the pharmaceutical composition.

Specifically, a content of water in the pharmaceutical composition of the present embodiment is preferably equal to or less than 5% by mass, more preferably equal to or less than 3% by mass, even more preferably equal to or less than 2% by mass, and particularly preferably equal to or less than 1% by mass, with respect to the entire mass of the pharmaceutical composition.

A content of the aqueous solvent in the pharmaceutical composition of the present embodiment is 15% by mass to 50% by mass with respect to the entire mass of the pharmaceutical composition.

In a case where the content of the aqueous solvent in the pharmaceutical composition of the present embodiment is equal to or greater than 15% by mass with respect to the entire mass of the pharmaceutical composition, good dissolution properties of fulvestrant are exhibited, and a pharmaceutical composition which contains fulvestrant at a high concentration, that is, at a concentration of equal to or greater than 8% by mass with respect to the entire mass of the pharmaceutical composition can be realized.

In a case where the content of the aqueous solvent in the pharmaceutical composition of the present embodiment is equal to or less than 50% by mass with respect to the entire mass of the pharmaceutical composition, it is possible to sufficiently secure a content of the nonaqueous carrier which is necessary to retain a therapeutically effective concentration of fulvestrant in blood for a certain period of time. Thus, in a case where, after intramuscular injection, the pharmaceutical composition is brought into contact with a body fluid and the aqueous solvent that has contributed to improvement of dissolution properties of fulvestrant in the pharmaceutical composition is caused to diffuse into the body fluid, there is a tendency that precipitation of fulvestrant becomes difficult to occur.

A content of the aqueous solvent in the pharmaceutical composition of the present embodiment is preferably 20% by mass to 40% by mass with respect to the entire mass of the pharmaceutical composition.

<Nonaqueous Carrier>

The pharmaceutical composition of the present embodiment contains a pharmaceutically acceptable nonaqueous carrier in an amount of 40% by mass to 75% by mass with respect to the entire mass of the pharmaceutical composition.

In addition, the nonaqueous carrier contained in the pharmaceutical composition of the present embodiment has a content of benzyl benzoate of less than 1% by mass with respect to the entire mass of the pharmaceutical composition.

In the pharmaceutical composition of the present embodiment, the nonaqueous carrier contributes to retaining a therapeutically effective concentration of fulvestrant in blood for a certain period of time.

In the present embodiment, the "nonaqueous carrier" means a pharmaceutically acceptable nonaqueous liquid substance, and, specifically, refers to a liquid substance having a solubility in water at 25° C. of less than 1% by mass.

The nonaqueous carrier is not particularly limited as long as the nonaqueous carrier is a pharmaceutically acceptable carrier.

As the nonaqueous carrier, vegetable oil, a nonaqueous ester compound, and the like are mentioned.

In the present embodiment, the "vegetable oil" means an oil and fat which is obtained by extraction from plant seeds, fruits, and the like, and, as the vegetable oil, vegetable oil that has been used as pharmaceutical additives is preferable.

As the vegetable oil, castor oil, sesame oil, peanut oil, soybean oil, camellia oil, corn oil, cottonseed oil, olive oil, safflower oil, rapeseed oil, medium-chain fatty acid triglyceride, and the like are mentioned. Here, the medium-chain fatty acid triglyceride means an oil and fat of which fatty acids (that is, constituent fatty acids) constituting triglyceride have 6 to 12 carbon atoms on average. The constituent fatty acid may be a saturated fatty acid or an unsaturated fatty acid. As the medium-chain fatty acid triglyceride, a triglyceride of a saturated fatty acid having 6 to 12 carbon atoms is preferable.

As the nonaqueous ester compound, benzyl benzoate, ethyl oleate, isopropyl myristate, diethyl sebacate, and the like are mentioned.

As the nonaqueous carrier, castor oil is preferable from the viewpoint that dissolution properties of fulvestrant and a sustained release of fulvestrant after intramuscular injection are good, and a mixture of castor oil and vegetable oil which is different from castor oil may be used.

As the vegetable oil which is different from castor oil, from the viewpoint that dissolution properties of fulvestrant and a sustained release of fulvestrant after intramuscular injection are better, at least one kind of vegetable oil selected from the group consisting of sesame oil, peanut oil, soybean oil, camellia oil, corn oil, cottonseed oil, olive oil, safflower oil, rapeseed oil, and a fatty acid triglyceride (that is, medium-chain fatty acid triglyceride) of which constituent fatty acids have 6 to 12 carbon atoms on average is preferable.

In addition, as the vegetable oil which is different from castor oil, from the viewpoint of having been used for injection solutions which are intramuscularly injected in Japan and foreign countries, at least one kind of vegetable oil selected from the group consisting of sesame oil, peanut oil, soybean oil, camellia oil, and corn oil is preferable, and, from the viewpoint of having been used for injection solutions which are intramuscularly injected in Japan, at least one kind of vegetable oil selected from sesame oil or peanut oil is more preferable.

In a case where the nonaqueous carrier contained in the pharmaceutical composition of the present embodiment is, for example, the mixture of castor oil and vegetable oil which is different from castor oil, types and contents of the vegetable oil which is different from castor oil are preferably set in consideration of a solubility of fulvestrant, from the viewpoint of achieving a good sustained release of fulvestrant after intramuscular injection.

For example, in a case where the nonaqueous carrier is the mixture of castor oil and vegetable oil which is different from castor oil, a solubility of fulvestrant in the nonaqueous carrier is preferably in a range of 0.70 to 1.0 in a case of setting a solubility of fulvestrant in castor oil to 1.0.

In the pharmaceutical composition of the present embodiment, in a case where the solubility of fulvestrant in the nonaqueous carrier is in the above range, it is possible to retain a therapeutically effective concentration of fulvestrant in blood for a certain period of time.

As used herein, the "solubility of fulvestrant" means a solubility at 37° C.

In the pharmaceutical composition of the present embodiment, it is preferable that the nonaqueous carrier further satisfies the following requirements (C) and (D).

(C) Castor oil is contained in an amount of equal to or greater than 40% by mass with respect to the entire mass of the pharmaceutical composition.

(D) A content of the vegetable oil which is different from castor oil is less than 20% by mass with respect to the entire mass of the pharmaceutical composition.

In the pharmaceutical composition of the present embodiment, in a case where the nonaqueous carrier further satisfies the above requirements (C) and (D), there is a tendency that precipitation of fulvestrant becomes more difficult to occur in a case of being brought into contact with a body fluid.

A content of benzyl benzoate in the pharmaceutical composition of the present embodiment is less than 1% by mass with respect to the entire mass of the pharmaceutical composition.

In a case where the content of benzyl benzoate in the pharmaceutical composition of the present embodiment is less than 1% by mass with respect to the entire mass of the pharmaceutical composition, even though the pharmaceutical composition contains fulvestrant at a high concentration, that is, at a concentration of equal to or greater than 8% by mass with respect to the entire mass of the pharmaceutical composition, there is a tendency that precipitation of fulvestrant becomes difficult to occur in a case of being brought into contact with a body fluid after intramuscular injection.

A content of benzyl benzoate in the pharmaceutical composition of the present embodiment is preferably less than 0.5% by mass, more preferably less than 0.3% by mass, and even more preferably less than 0.1% by mass, with respect to the entire mass of the pharmaceutical composition, and particularly preferably benzyl benzoate is not contained, that is, 0% by mass.

In the pharmaceutical composition of the present embodiment, a content of the nonaqueous carrier is 40% by mass to 75% by mass with respect to the entire mass of the pharmaceutical composition.

In a case where the content of the nonaqueous carrier in the pharmaceutical composition of the present embodiment is equal to or greater than 40% by mass with respect to the entire mass of the pharmaceutical composition, it is possible to retain a therapeutically effective concentration of fulvestrant in blood for a certain period of time, and there is a tendency that precipitation of fulvestrant becomes difficult to occur in a case where, after intramuscular injection, the pharmaceutical composition is brought into contact with a body fluid and the aqueous solvent that has contributed to improvement of dissolution properties of fulvestrant in the pharmaceutical composition is caused to diffuse into the body fluid.

In a case where the content of the nonaqueous carrier in the pharmaceutical composition of the present embodiment is equal to or less than 75% by mass with respect to the entire mass of the pharmaceutical composition, it is possible to secure a content of the aqueous solvent which is necessary to increase dissolution properties of fulvestrant in the pharmaceutical composition.

The content of the nonaqueous carrier in the pharmaceutical composition of the present embodiment is preferably 50% by mass to 70% by mass, and more preferably 55% by mass to 70% by mass, with respect to the entire mass of the pharmaceutical composition.

In addition to fulvestrant, the aqueous solvent, and the pharmaceutically acceptable nonaqueous carrier, the pharmaceutical composition of the present embodiment may, if necessary, further contain a pharmaceutically acceptable additive (hereinafter referred to as "other additive"). In a case where the pharmaceutical composition of the present embodiment is applied for intramuscular injection, it is preferable to further contain an additive suitable for intramuscular injection.

As the other additive, glycerin, ascorbic acid or a salt thereof, hydrochloric acid, gluconic acid or a salt thereof, acetic acid or a salt thereof, lactic acid or a salt thereof, boric acid or a salt thereof, phosphoric acid or a salt thereof, sulfuric acid or a salt thereof, tartaric acid or a salt thereof, citric acid or a salt thereof, potassium hydroxide, calcium hydroxide, sodium hydroxide, magnesium hydroxide, monoethanolamine, diethanolamine, triethanolamine, trometamol, meglumine, glycine, histidine or a salt thereof, ε-aminocaproic acid, arginine or a salt thereof, cysteine or a salt thereof, methionine, alanine, leucine, aspartic acid or a salt thereof, glutamic acid or a salt thereof, thioglycerin, thioglycolic acid or a salt thereof, taurine, sodium edetate, lidocaine or a salt thereof, nicotinic acid amide, chlorobutanol, creatinine, butylhydroxytoluene, butylhydroxyanisole, sorbitan sesquioleic acid ester, ethyl oleate, ethyl lactate, tyromesal, polyoxyethylene hardened castor oil, polysorbate 20, polysorbate 80, and the like are mentioned.

However, the other additive is not limited thereto.

In a case where the pharmaceutical composition of the present embodiment contains the other additives, the pharmaceutical composition may contain only one type of the other additives or may contain two or more types thereof.

In a case where the pharmaceutical composition of the present embodiment contains the other additive, a content of the other additive in the pharmaceutical composition is preferably equal to or less than 10% by mass, more preferably equal to or less than 5% by mass, and even more preferably equal to or less than 3% by mass, with respect to the entire mass of the pharmaceutical composition.

As preferable compositional examples of the pharmaceutical composition of the present embodiment, for example, the following compositions are mentioned. In the pharmaceutical composition of the present embodiment having a composition shown below, precipitation of fulvestrant becomes more difficult to occur in a case of being brought into contact with a body fluid after intramuscular injection.

A composition that contains fulvestrant, an aqueous solvent, and a pharmaceutically acceptable nonaqueous carrier, in which a content of fulvestrant is equal to or greater than 8% by mass (more preferably 8% by mass to 12% by mass) with respect to the entire mass of the pharmaceutical composition, the aqueous solvent satisfies the following requirements (i) to (iv), and the pharmaceutically acceptable nonaqueous carrier satisfies the following requirements (a) to (d).

(i) Ethanol is contained in an amount of 10% by mass to 20% by mass with respect to the entire mass of the pharmaceutical composition.

(ii) Propylene glycol is contained in an amount of 10% by mass to 20% by mass with respect to the entire mass of the pharmaceutical composition.

(iii) A content of benzyl alcohol is less than 5% by mass with respect to the entire mass of the pharmaceutical composition.

(iv) A content of the aqueous solvent is 20% by mass to 40% by mass with respect to the entire mass of the pharmaceutical composition.

(a) A content of benzyl benzoate is less than 1% by mass with respect to the entire mass of the pharmaceutical composition.

(b) Castor oil is contained in an amount of equal to or greater than 40% by mass with respect to the entire mass of the pharmaceutical composition.

(c) A content of at least one kind of vegetable oil selected from sesame oil or peanut oil is less than 20% by mass with respect to the entire mass of the pharmaceutical composition.

(d) A content of the pharmaceutically acceptable nonaqueous carrier is 40% by mass to 75% by mass with respect to the entire mass of the pharmaceutical composition.

[Use of Pharmaceutical Composition]

The pharmaceutical composition of the present embodiment can be suitably used for intramuscular injection.

According to the pharmaceutical composition of the present embodiment, the fulvestrant is contained at a high concentration (for example, a concentration of equal to or greater than 8% by mass with respect to the entire mass of the pharmaceutical composition), and precipitation of fulvestrant becomes difficult to occur in a case of being brought into contact with a body fluid after intramuscular injection. Thus, it is possible to reduce injection sites from two locations in the related art to one location, or to reduce a dose per injection site, which makes it possible to reduce a burden on patients. In addition, the pharmaceutical composition of the present embodiment is a pharmaceutical preparation suitable for intramuscular injection from the viewpoints that good dissolution properties of fulvestrant are exhibited, phase separation or precipitation becomes difficult to occur in ingredients contained in the pharmaceutical composition even in a case of being stored at a low temperature, and a state in which ingredients such as fulvestrant are well mixed is stably retained.

In addition, since the pharmaceutical composition of the present embodiment contains fulvestrant as an active ingredient, the pharmaceutical composition can be suitably used for the treatment of breast cancer, uterine myoma, and endometriosis.

[Method for Producing Pharmaceutical Composition]

A method for producing the pharmaceutical composition of the present embodiment is not particularly limited as long as the method is capable of producing the aforementioned pharmaceutical composition.

As the method for producing the pharmaceutical composition of the present embodiment, from the viewpoint that it is easy to obtain a pharmaceutical composition in which ingredients contained therein are uniformly mixed, a method for producing the pharmaceutical composition of the present embodiment, which will be described below, is preferable.

A method for producing the pharmaceutical composition of the present embodiment (hereinafter also referred to as "production method of the present embodiment") has a step (hereinafter also referred to as "first step") of mixing fulvestrant, ethanol, and at least one kind of polyhydric alcohol (specific polyhydric alcohol) selected from propylene glycol or 1,3-butylene glycol, to obtain a dissolution liquid of fulvestrant, and a step (hereinafter also referred to as "second step") of mixing the obtained dissolution liquid of fulvestrant with a pharmaceutically acceptable nonaqueous carrier, to obtain a pharmaceutical composition.

The production method of the present embodiment has an advantage that it is easy to obtain a pharmaceutical composition in which ingredients contained therein are uniformly mixed, as compared with a case where fulvestrant, ethanol, the specific polyhydric alcohol, and the pharmaceutically acceptable nonaqueous carrier are mixed all together.

Hereinafter, the production method of the present embodiment will be described. However, descriptions regarding matters which are common to the above-described pharmaceutical composition, for example, ingredients contained in the pharmaceutical composition and amounts thereof will be omitted.

<First Step>

The first step is a step of mixing fulvestrant, ethanol, and a specific polyhydric alcohol, to obtain a dissolution liquid of fulvestrant.

In a case where the above-described pharmaceutical composition contains the other additive, it is preferable that fulvestrant, ethanol, the specific polyhydric alcohol, and the other additive are mixed to obtain a dissolution liquid of fulvestrant.

In the first step, it is sufficient that the respective ingredients to be mixed are simply mixed, in which all the ingredients may be mixed at one time, or the respective ingredients may be divided into several portions and mixed.

A method of mixing is not particularly limited, and, for example, mixing by stirring is mentioned.

A temperature condition at the time of mixing is not particularly limited, and can be appropriately set, for example, according to a composition (types and amounts) of the ingredients to be mixed and the like.

In the first step, usually, fulvestrant, ethanol, and the specific polyhydric alcohol are mixed under a condition of an atmospheric temperature of 15° C. to 60° C., to obtain a dissolution liquid of fulvestrant.

<Second Step>

The second step is a step of mixing the dissolution liquid of fulvestrant obtained in the first step and the pharmaceutically acceptable nonaqueous carrier (for example, castor oil), to obtain a pharmaceutical composition.

A method of mixing is not particularly limited, and, for example, mixing by stirring is mentioned.

In the second step, the dissolution liquid of fulvestrant and the pharmaceutically acceptable nonaqueous carrier may be mixed at one time, or, for example, the dissolution liquid of fulvestrant and the pharmaceutically acceptable nonaqueous carrier may be mixed by gradually adding the pharmaceutically acceptable nonaqueous carrier to the dissolution liquid of fulvestrant while stirring the dissolution liquid of fulvestrant.

A temperature condition at the time of mixing is not particularly limited.

In the second step, usually, the dissolution liquid of fulvestrant and the pharmaceutically acceptable nonaqueous carrier are mixed under a condition of an atmospheric temperature of 15° C. to 60° C., to obtain a pharmaceutical composition.

<Other Step>

The production method of the present embodiment may, if necessary, have another step than the first step and the second step. In addition, the first step and the second step may be configured to include a plurality of steps.

As the other step, a step of sterilizing the pharmaceutical composition, a step of filling a container with the pharmaceutical composition, and the like are mentioned.

As the sterilizing step, a filter sterilization method using a sterilizing filter is preferable.

[Container for Pharmaceutical Composition]

As a container which is to be filled with the pharmaceutical composition of the present embodiment, a vial, an ampoule, a syringe, and the like are mentioned.

Among these, as the container which is to be filled with the pharmaceutical composition of the present embodiment, from the viewpoint of handleability in a medical field, a syringe is preferable, and a glass syringe is more preferable. That is, as a dosage form of the pharmaceutical composition of the present embodiment, a prefilled syringe obtained by previously filling a syringe with a pharmaceutical composition is preferable.

[Others]

Another embodiment of the present invention also encompasses a method for the treatment of breast cancer, which includes administering, to a patient to be treated for breast cancer, the above-described pharmaceutical composition containing fulvestrant as an active ingredient.

In addition, yet another embodiment of the present invention also encompasses a method for the treatment of uterine myoma which includes administering, to a patient to be treated for uterine myoma, the above-described pharmaceutical composition containing fulvestrant as an active ingredient.

Furthermore, still yet another embodiment of the present invention also encompasses a method for the treatment of endometriosis which includes administering, to a patient to be treated for endometriosis, the above-described pharmaceutical composition containing fulvestrant as an active ingredient.

EXAMPLES

Hereinafter, the present invention will be described in more detail by way of Examples. However, the present invention is not limited to the following Examples to the extent that the present invention does not deviate from a spirit thereof.

[Production of Pharmaceutical Composition]

Example 1

10 parts by mass of fulvestrant, 11 parts by mass of ethanol, and 14 parts by mass of propylene glycol (PG) as a specific polyhydric alcohol were weighed into a clean glass container containing a stirring bar. Then, the mixture was stirred to dissolve fulvestrant, and a dissolution liquid of fulvestrant was obtained. Subsequently, castor oil was added to the obtained dissolution liquid of fulvestrant so that a total amount was adjusted to 100 parts by mass. Then, the mixture was further stirred to become uniform, and a pharmaceutical composition of Example 1 was obtained.

Examples 2 to 53, 101, and 102, and Comparative Examples 1 to 66 and 101

By carrying out the same operation as in Example 1, except that the composition of the pharmaceutical composition was changed to each of compositions shown in Tables 1 to 10, pharmaceutical compositions of Examples 2 to 53, 101, and 102, and Comparative Examples 1 to 66 and 101 were obtained.

[Evaluation]
1. Presence or Absence of Turbidity

Regarding each of the pharmaceutical compositions of Examples 1 to 53, 101, and 102, and Comparative Examples 1 to 66 and 101 as obtained above, at least 1 mL thereof was weighed and taken into each colorless transparent glass bottle (5 mL volume), and stored in a refrigerator (atmospheric temperature: 2° C. to 8° C.). After 1 hour or longer had passed from the start of storage, the glass bottle was taken out from the refrigerator. Immediately after being taken out, cloudiness formed on a surface of the glass bottle was wiped off with Kimwipe (registered trademark), and then the pharmaceutical composition placed in the glass bottle was visually observed to identify presence or absence of turbidity. The results are shown in Tables 1 to 10.

In Tables 1 to 10, a case where turbidity is not identified in the pharmaceutical composition placed in the glass bottle was denoted as "absent", and a case where turbidity is identified was denoted as "present".

In the above evaluation, a state in which turbidity is not identified in the pharmaceutical composition placed in the glass bottle (that is, the pharmaceutical composition is clear) indicates a state in which the ingredients contained therein are uniformly mixed, meaning that no phase separation or precipitation occurs in the ingredients contained in the pharmaceutical composition during storage at a low temperature (2° C. to 8° C.), and a state in which the ingredients such as fulvestrant are well mixed is stably retained.

On the other hand, a state in which turbidity is identified in the pharmaceutical composition contained in the glass bottle indicates a state in which the ingredients contained therein are not uniformly mixed, meaning that any of the ingredients contained in the pharmaceutical composition is phase-separated or precipitated during storage at a low temperature (2° C. to 8° C.), and the pharmaceutical composition is not a preparation suitable for intramuscular injection.

2. Dissolution Properties of Fulvestrant

To each of the pharmaceutical compositions of Examples 1 to 53, 101, and 102, and Comparative Examples 1 to 66 and 101 as obtained above, at least a saturated amount of fulvestrant was further added, and the mixture was stirred under a condition of 15° C. to 30° C. for at least one day. Then, the mixture was centrifuged at a condition of 10,000 or higher round per minute (rpm) and 10 minutes or longer to remove an excess of fulvestrant, and a supernatant was obtained.

An amount of fulvestrant dissolved in the obtained supernatant was measured by high performance liquid chromatography (HPLC) under the following conditions to calculate a solubility (% by mass) of fulvestrant.

Then, based on Equation (I), a dissolution rate (% by mass) was calculated and the dissolution properties of fulvestrant were evaluated according to the following evaluation standard.

Dissolution rate (% by mass)=[blending amount (% by mass) of fulvestrant charged at time of producing pharmaceutical composition]/[solubility (% by mass) of fulvestrant]×100  Equation (I)

A lower dissolution rate of fulvestrant indicates that the pharmaceutical composition has a higher ability to sufficiently and uniformly contain fulvestrant which is necessary for treatment.

In a case where an evaluation result was "A", "B", or "C", the pharmaceutical composition was determined as acceptable.

~Evaluation Standard~

A: Dissolution rate is equal to or less than 70% by mass.

B: Dissolution rate is greater than 70% by mass and equal to or less than 80% by mass.

C: Dissolution rate is greater than 80% by mass and equal to or less than 90% by mass.

D: Dissolution rate is greater than 90% by mass.

—HPLC Conditions—

Column:)(Bridge C8 (product name, particle diameter: 3.5 μm, column size: 4.6 mm×150 mm, Waters Corporation)

Mobile phase A: methanol/water=70/30

Mobile phase B: Methanol

Gradient condition (proportion of mobile phase B): 0% (start)→0% (12 min)→100% (12.1 min)→100% (20 min)→0% (20.1 min)→0% (30 min, stop)

Detection wavelength: 225 nm

Flow rate: 1.0 mL/min

Column temperature: 40° C.

3. Precipitation Properties

Among the pharmaceutical compositions of Examples 1 to 53, 101, and 102, and Comparative Examples 1 to 66 and 101 as obtained above, for those in which turbidity was not identified in the evaluation test for 1. presence or absence of turbidity, and the solubility of fulvestrant was equal to or greater than 10.0% by mass in the evaluation test for 2. dissolution properties of fulvestrant, precipitation properties were evaluated.

An evaluation test for the precipitation properties is aimed at identifying whether fulvestrant in a pharmaceutical composition is precipitated in a case where the pharmaceutical composition is brought into contact with a body fluid. The evaluation test was performed by a model experiment using a physiological saline solution which shows almost the same osmotic pressure as an osmotic pressure of a human body fluid, instead of a human body fluid.

For each pharmaceutical composition, an amount containing 50 mg of fulvestrant (for example, 0.5 mL in a case of the pharmaceutical composition of Example 1) was weighed and taken, and gently added dropwise to 20 mL of a physiological saline solution placed in a colorless transparent glass bottle (30 mL volume). Subsequently, the glass bottle was hermetically capped, and allowed to stand in a thermostatic chamber at 25° C. for 3 days. Then, an oil phase (that is, a phase including the nonaqueous carrier of the pharmaceutical composition) was recovered, and a state of the oil phase was visually observed to identify the presence or absence of precipitation and the state thereof. The results are shown in Tables 1 to 10.

In Tables 1 to 10, a case where precipitation is not identified in the oil phase was denoted as "A", a case where precipitation is slightly identified was denoted as "B", and a case where precipitation was remarkably identified was denoted as "C". In a case of "A" or "B", there is no problem for practical use.

The recovered oil phase was centrifuged under a condition of 10,000 or higher rpm and 10 minutes or longer to obtain a supernatant. The obtained supernatant was analyzed by HPLC to measure a concentration A (mg/g) of fulvestrant dissolved in the oil phase, and a dissolution rate (% by mass) in the oil phase was calculated based on Equation (1). The HPLC analysis was carried out at conditions similar to the HPLC conditions in 2. dissolution properties of fulvestrant. The results are shown in Tables 1 to 10.

Oil phase dissolution rate (% by mass)=[concentration A (mg/g) of fulvestrant dissolved in oil phase measured by HPLC analysis]/[concentration B (mg/g) of fulvestrant in oil phase in case where entire fulvestrant is dissolved]×100    Equation (1)

The concentration B (mg/g) of fulvestrant in the oil phase in a case where the entire fulvestrant is dissolved was calculated based on Equation (2).

Concentration B (mg/g) of fulvestrant in oil phase= [content (% by mass) of fulvestrant in pharmaceutical composition]×1000/[[content (% by mass) of fulvestrant in pharmaceutical composition]+[total content (% by mass) of nonaqueous carrier in pharmaceutical composition]]    Equation (2)

In the above evaluation, approaching of the oil phase dissolution rate to 100% by mass indicates that precipitation of fulvestrant becomes difficult to occur in an oil phase after the pharmaceutical composition is added dropwise to a physiological saline solution, and a state (a so-called supersaturated state) in which fulvestrant is dissolved beyond an original solubility thereof is sufficiently maintained.

In a case where the oil phase dissolution rate is equal to or greater than 70% by mass, it was determined that precipitation is sufficiently suppressed.

In Tables 1 to 10, a case where the oil phase dissolution rate is equal to or greater than 70% by mass was denoted as "good", and a case where the oil phase dissolution rate is less than 70% by mass was denoted as "poor".

TABLE 1

|  | | Aqueous solvent (% by mass) | | | | Nonaqueous carrier (% by mass) | | | | Evaluation test | |
| --- | --- | --- | --- | --- | --- | --- | --- | --- | --- | --- | --- |
|  | FLV (% by mass) | EtOH | PG | BnOH | Total amount | BnBz | Sesame oil | Castor oil | Total amount | Presence or absence of turbidity | Dissolution properties Solubility (% by mass) |
| Example 1 | 10 | 11 | 14 | 0 | 25 | 0 | 0 | 65 | 65 | Absent | 14.9 |
| Example 2 | 10 | 20 | 5 | 0 | 25 | 0 | 0 | 65 | 65 | Absent | 19.9 |
| Example 3 | 10 | 15 | 10 | 0 | 25 | 0 | 0 | 65 | 65 | Absent | 16.7 |
| Comparative Example 1 | 10 | 5 | 20 | 0 | 25 | 0 | 0 | 65 | 65 | Present | 10.6 |
| Comparative Example 2 | 10 | 20 | 0 | 5 | 25 | 0 | 0 | 65 | 65 | Absent | 15.2 |
| Comparative Example 3 | 10 | 15 | 5 | 5 | 25 | 0 | 0 | 65 | 65 | Absent | 12.6 |
| Comparative Example 4 | 10 | 15 | 0 | 10 | 25 | 0 | 0 | 65 | 65 | Absent | 10.9 |
| Comparative Example 5 | 10 | 10 | 0 | 15 | 25 | 0 | 0 | 65 | 65 | Present | 8.4 |
| Comparative Example 6 | 10 | 10 | 5 | 10 | 25 | 0 | 0 | 65 | 65 | Present | 9.2 |
| Comparative Example 7 | 10 | 10 | 10 | 5 | 25 | 0 | 0 | 65 | 65 | Absent | 10.0 |
| Comparative Example 8 | 10 | 5 | 0 | 20 | 25 | 0 | 0 | 65 | 65 | Present | 5.7 |
| Comparative Example 9 | 10 | 5 | 5 | 15 | 25 | 0 | 0 | 65 | 65 | Present | 6.1 |
| Comparative Example 10 | 10 | 5 | 10 | 10 | 25 | 0 | 0 | 65 | 65 | Present | 5.9 |
| Comparative Example 11 | 10 | 5 | 15 | 5 | 25 | 0 | 0 | 65 | 65 | Present | 7.3 |
| Comparative Example 12 | 10 | 0 | 5 | 20 | 25 | 0 | 0 | 65 | 65 | Present | 4.1 |
| Comparative Example 13 | 10 | 0 | 10 | 15 | 25 | 0 | 0 | 65 | 65 | Present | 4.5 |
| Comparative Example 14 | 10 | 0 | 15 | 10 | 25 | 0 | 0 | 65 | 65 | Present | 4.8 |
| Comparative Example 15 | 10 | 0 | 20 | 5 | 25 | 0 | 0 | 65 | 65 | Present | 5.5 |
| Example 4 | 10 | 13 | 10 | 2 | 25 | 0 | 0 | 65 | 65 | Absent | 14.4 |
| Example 5 | 10 | 18 | 5 | 2 | 25 | 0 | 0 | 65 | 65 | Absent | 14.9 |
| Example 6 | 10 | 8 | 17 | 0 | 25 | 0 | 0 | 65 | 65 | Absent | 12.5 |
| Example 7 | 10 | 12 | 10 | 3 | 25 | 0 | 0 | 65 | 65 | Absent | 12.5 |
| Example 8 | 10 | 17 | 5 | 3 | 25 | 0 | 0 | 65 | 65 | Absent | 15.0 |

TABLE 1-continued

|  |  | Evaluation test | | | | | |
|---|---|---|---|---|---|---|---|
|  |  | Dissolution properties | | Precipitation properties | | | |
|  |  | Dissolution rate (% by mass) | Evaluation | Identification of precipitation | Oil phase dissolution rate (% by mass) | Evaluation | Overall evaluation |
|  | Example 1 | 67 | A | A | 97 | Good | AAA |
|  | Example 2 | 50 | A | A | 97 | Good | AAA |
|  | Example 3 | 60 | A | A | 97 | Good | AAA |
|  | Comparative Example 1 | 94 | D | A | 90 | Good | D |
|  | Comparative Example 2 | 66 | A | C | 47 | Poor | D |
|  | Comparative Example 3 | 79 | B | C | 34 | Poor | D |
|  | Comparative Example 4 | 92 | D | C | 26 | Poor | D |
|  | Comparative Example 5 | >100 | D | NT | NT | — | D |
|  | Comparative Example 6 | >100 | D | NT | NT | — | D |
|  | Comparative Example 7 | >100 | D | C | 30 | Poor | D |
|  | Comparative Example 8 | >100 | D | NT | NT | — | D |
|  | Comparative Example 9 | >100 | D | NT | NT | — | D |
|  | Comparative Example 10 | >100 | D | NT | NT | — | D |
|  | Comparative Example 11 | >100 | D | NT | NT | — | D |
|  | Comparative Example 12 | >100 | D | NT | NT | — | D |
|  | Comparative Example 13 | >100 | D | NT | NT | — | D |
|  | Comparative Example 14 | >100 | D | NT | NT | — | D |
|  | Comparative Example 15 | >100 | D | NT | NT | — | D |
|  | Example 4 | 69 | A | A | 91 | Good | AAA |
|  | Example 5 | 67 | A | A | 87 | Good | B |
|  | Example 6 | 80 | B | A | 97 | Good | AA |
|  | Example 7 | 80 | B | B | 79 | Good | C |
|  | Example 8 | 67 | A | B | 80 | Good | B |

TABLE 2

|  | FLV (% by mass) | Aqueous solvent (% by mass) | | | | Nonaqueous carrier (% by mass) | | | | Evaluation test | |
|---|---|---|---|---|---|---|---|---|---|---|---|
|  |  | EtOH | PG | BnOH | Total amount | BnBz | Sesame oil | Castor oil | Total amount | Presence or absence of turbidity | Dissolution properties Solubility (% by mass) |
| Example 9 | 10 | 15 | 20 | 0 | 35 | 0 | 0 | 55 | 55 | Absent | 19.8 |
| Example 10 | 10 | 28 | 7 | 0 | 35 | 0 | 0 | 55 | 55 | Absent | 20.6 |
| Example 11 | 10 | 21 | 14 | 0 | 35 | 0 | 0 | 55 | 55 | Absent | 19.9 |
| Comparative Example 16 | 10 | 7 | 28 | 0 | 35 | 0 | 0 | 55 | 55 | Present | NT |
| Comparative Example 17 | 10 | 28 | 0 | 7 | 35 | 0 | 0 | 55 | 55 | Absent | 20.1 |
| Comparative Example 18 | 10 | 21 | 7 | 7 | 35 | 0 | 0 | 55 | 55 | Absent | 18.0 |
| Comparative Example 19 | 10 | 21 | 0 | 14 | 35 | 0 | 0 | 55 | 55 | Absent | 16.6 |
| Comparative Example 20 | 10 | 14 | 0 | 21 | 35 | 0 | 0 | 55 | 55 | Absent | 12.9 |
| Comparative Example 21 | 10 | 14 | 7 | 14 | 35 | 0 | 0 | 55 | 55 | Absent | 12.8 |
| Comparative Example 22 | 10 | 14 | 14 | 7 | 35 | 0 | 0 | 55 | 55 | Absent | 13.4 |

TABLE 2-continued

| | | | | | | | | | | | |
|---|---|---|---|---|---|---|---|---|---|---|---|
| Comparative Example 23 | 10 | 7 | 0 | 28 | 35 | 0 | 0 | 55 | 55 | Present | 9.8 |
| Comparative Example 24 | 10 | 7 | 7 | 21 | 35 | 0 | 0 | 55 | 55 | Present | 9.9 |
| Comparative Example 25 | 10 | 7 | 14 | 14 | 35 | 0 | 0 | 55 | 55 | Present | 9.7 |
| Comparative Example 26 | 10 | 7 | 21 | 7 | 35 | 0 | 0 | 55 | 55 | Present | 9.6 |
| Comparative Example 27 | 10 | 0 | 7 | 28 | 35 | 0 | 0 | 55 | 55 | Present | 6.6 |
| Comparative Example 28 | 10 | 0 | 14 | 21 | 35 | 0 | 0 | 55 | 55 | Present | 6.6 |

| | Evaluation test | | | | | |
|---|---|---|---|---|---|---|
| | Dissolution properties | | Precipitation properties | | | |
| | Dissolution rate (% by mass) | Evaluation | Identification of precipitation | Oil phase dissolution rate (% by mass) | Evaluation | Overall evaluation |
| Example 9 | 50 | A | A | 96 | Good | AAA |
| Example 10 | 49 | A | A | 96 | Good | AAA |
| Example 11 | 50 | A | A | 96 | Good | AAA |
| Comparative Example 16 | NT | — | NT | NT | — | D |
| Comparative Example 17 | 50 | A | C | 24 | Poor | D |
| Comparative Example 18 | 55 | A | C | 23 | Poor | D |
| Comparative Example 19 | 60 | A | C | 22 | Poor | D |
| Comparative Example 20 | 77 | B | C | 23 | Poor | D |
| Comparative Example 21 | 78 | B | C | 22 | Poor | D |
| Comparative Example 22 | 75 | B | C | 22 | Poor | D |
| Comparative Example 23 | >100 | D | NT | NT | — | D |
| Comparative Example 24 | >100 | D | NT | NT | — | D |
| Comparative Example 25 | >100 | D | NT | NT | — | D |
| Comparative Example 26 | >100 | D | NT | NT | — | D |
| Comparative Example 27 | >100 | D | NT | NT | — | D |
| Comparative Example 28 | >100 | D | NT | NT | — | D |

TABLE 3

| | FLV (% by mass) | Aqueous solvent (% by mass) | | | | Nonaqueous carrier (% by mass) | | | | Evaluation test | |
|---|---|---|---|---|---|---|---|---|---|---|---|
| | | EtOH | PG | BnOH | Total amount | BnBz | Sesame oil | Castor oil | Total amount | Presence or absence of turbidity | Dissolution properties Solubility (% by mass) |
| Comparative Example 29 | 10 | 7 | 8 | 0 | 15 | 0 | 0 | 75 | 75 | Present | 9.0 |
| Example 12 | 10 | 12 | 3 | 0 | 15 | 0 | 0 | 75 | 75 | Absent | 11.8 |
| Comparative Example 30 | 10 | 9 | 0 | 6 | 15 | 0 | 0 | 75 | 75 | Present | 6.4 |
| Comparative Example 31 | 10 | 6 | 6 | 3 | 15 | 0 | 0 | 75 | 75 | Present | 6.5 |
| Comparative Example 32 | 10 | 11 | 4 | 5 | 20 | 0 | 0 | 70 | 70 | Present | 9.7 |
| Example 13 | 10 | 16 | 4 | 0 | 20 | 0 | 0 | 70 | 70 | Absent | 16.4 |
| Comparative Example 33 | 10 | 7 | 8 | 5 | 20 | 0 | 0 | 70 | 70 | Present | 8.0 |

TABLE 3-continued

| | | | | | | | | | | | |
|---|---|---|---|---|---|---|---|---|---|---|---|
| Example 14 | 10 | 12 | 8 | 0 | 20 | 0 | 0 | 70 | 70 | Absent | 14.3 |
| Comparative Example 34 | 10 | 5 | 12 | 3 | 20 | 0 | 0 | 70 | 70 | Present | 7.8 |
| Example 15 | 10 | 8 | 12 | 0 | 20 | 0 | 0 | 70 | 70 | Absent | 12.1 |
| Example 16 | 10 | 14 | 4 | 2 | 20 | 0 | 0 | 70 | 70 | Absent | 13.2 |
| Example 17 | 10 | 15 | 4 | 1 | 20 | 0 | 0 | 70 | 70 | Absent | 14.7 |
| Example 18 | 10 | 11 | 8 | 1 | 20 | 0 | 0 | 70 | 70 | Absent | 12.6 |
| Comparative Example 35 | 10 | 6 | 12 | 2 | 20 | 0 | 0 | 70 | 70 | Present | 8.9 |
| Comparative Example 36 | 10 | 7 | 12 | 1 | 20 | 0 | 0 | 70 | 70 | Present | 10.2 |

| | Evaluation test | | | | | |
|---|---|---|---|---|---|---|
| | Dissolution properties | | Precipitation properties | | | |
| | Dissolution rate (% by mass) | Evaluation | Identification of precipitation | Oil phase dissolution rate (% by mass) | Evaluation | Overall evaluation |
| Comparative Example 29 | >100 | D | NT | NT | — | D |
| Example 12 | 85 | C | A | 96 | Good | A |
| Comparative Example 30 | >100 | D | NT | NT | — | D |
| Comparative Example 31 | >100 | D | NT | NT | — | D |
| Comparative Example 32 | >100 | D | NT | NT | — | D |
| Example 13 | 61 | A | A | 103 | Good | AAA |
| Comparative Example 33 | >100 | D | NT | NT | — | D |
| Example 14 | 70 | A | A | 101 | Good | AAA |
| Comparative Example 34 | >100 | D | NT | NT | — | D |
| Example 15 | 83 | C | A | 102 | Good | A |
| Example 16 | 76 | B | A | 91 | Good | AA |
| Example 17 | 68 | A | A | 99 | Good | AAA |
| Example 18 | 79 | B | A | 98 | Good | AA |
| Comparative Example 35 | >100 | D | NT | NT | — | D |
| Comparative Example 36 | 98 | D | NT | NT | — | D |

TABLE 4

| | FLV (% by mass) | Aqueous solvent (% by mass) | | | | Nonaqueous carrier (% by mass) | | | | Evaluation test | |
|---|---|---|---|---|---|---|---|---|---|---|---|
| | | EtOH | PG | BnOH | Total amount | BnBz | Sesame oil | Castor oil | Total amount | Presence or absence of turbidity | Dissolution properties Solubility (% by mass) |
| Comparative Example 37 | 10 | 16 | 14 | 5 | 35 | 0 | 0 | 55 | 55 | Absent | 16.9 |
| Comparative Example 38 | 10 | 10 | 20 | 5 | 35 | 0 | 0 | 55 | 55 | Absent | 13.4 |
| Comparative Example 39 | 10 | 23 | 7 | 5 | 35 | 0 | 0 | 55 | 55 | Absent | 20.6 |
| Comparative Example 40 | 10 | 11 | 14 | 0 | 25 | 1 | 0 | 64 | 65 | Absent | 12.2 |
| Comparative Example 41 | 10 | 11 | 14 | 0 | 25 | 3 | 0 | 62 | 65 | Absent | 10.6 |
| Comparative Example 42 | 10 | 11 | 14 | 0 | 25 | 5 | 0 | 60 | 65 | Absent | 10.6 |
| Comparative Example 43 | 10 | 11 | 14 | 0 | 25 | 10 | 0 | 55 | 65 | Absent | 10.6 |
| Comparative Example 44 | 10 | 11 | 14 | 0 | 25 | 15 | 0 | 50 | 65 | Absent | 11.1 |

TABLE 4-continued

| | | Evaluation test | | | | | |
|---|---|---|---|---|---|---|---|
| | | Dissolution properties | | Precipitation properties | | | |
| | | Dissolution rate (% by mass) | Evaluation | Identification of precipitation | Oil phase dissolution rate (% by mass) | Evaluation | Overall evaluation |
| | Comparative Example 37 | 59 | A | C | 25 | Poor | D |
| | Comparative Example 38 | 75 | B | C | 25 | Poor | D |
| | Comparative Example 39 | 49 | A | C | 25 | Poor | D |
| | Comparative Example 40 | 82 | C | C | 43 | Poor | D |
| | Comparative Example 41 | 94 | D | C | 21 | Poor | D |
| | Comparative Example 42 | 94 | D | C | 19 | Poor | D |
| | Comparative Example 43 | 94 | D | C | 18 | Poor | D |
| | Comparative Example 44 | 90 | C | C | 18 | Poor | D |

TABLE 5

| | FLV (% by mass) | Aqueous solvent (% by mass) | | | | Nonaqueous carrier (% by mass) | | | | Evaluation test | |
|---|---|---|---|---|---|---|---|---|---|---|---|
| | | EtOH | PG | BnOH | Total amount | BnBz | Sesame oil | Castor oil | Total amount | Presence or absence of turbidity | Dissolution properties Solubility (% by mass) |
| Example 19 | 10 | 11 | 14 | 0 | 25 | 0 | 2.5 | 62.5 | 65 | Absent | 14.6 |
| Example 20 | 10 | 11 | 14 | 0 | 25 | 0 | 5 | 60 | 65 | Absent | 14.3 |
| Example 21 | 10 | 15 | 10 | 0 | 25 | 0 | 5 | 60 | 65 | Absent | 17.7 |
| Example 22 | 10 | 15 | 10 | 0 | 25 | 0 | 10 | 55 | 65 | Absent | 16.0 |

| | | Evaluation test | | | | | |
|---|---|---|---|---|---|---|---|
| | | Dissolution properties | | Precipitation properties | | | |
| | | Dissolution rate (% by mass) | Evaluation | Identification of precipitation | Oil phase dissolution rate (% by mass) | Evaluation | Overall evaluation |
| | Example 19 | 68 | A | A | 100 | Good | AAA |
| | Example 20 | 70 | A | A | 100 | Good | AAA |
| | Example 21 | 56 | A | A | 99 | Good | AAA |
| | Example 22 | 63 | A | A | 91 | Good | AAA |

TABLE 6

| | FLV (% by mass) | Aqueous solvent (% by mass) | | | | Nonaqueous carrier (% by mass) | | | | Evaluation test | |
|---|---|---|---|---|---|---|---|---|---|---|---|
| | | EtOH | PG | BnOH | Total amount | BnBz | Sesame oil | Castor oil | Total amount | Presence or absence of turbidity | Dissolution properties Solubility (% by mass) |
| Example 23 | 10 | 10 | 15 | 0 | 25 | 0 | 0 | 65 | 65 | Absent | 14.6 |
| Example 24 | 10 | 16 | 24 | 0 | 40 | 0 | 0 | 50 | 50 | Absent | 21.6 |
| Example 25 | 10 | 20 | 30 | 0 | 50 | 0 | 0 | 40 | 40 | Absent | 25.0 |
| Comparative Example 45 | 10 | 24 | 36 | 0 | 60 | 0 | 0 | 30 | 30 | Absent | 28.4 |

TABLE 6-continued

| | | | | | | | | | | | |
|---|---|---|---|---|---|---|---|---|---|---|---|
| Example 26 | 10 | 15 | 10 | 0 | 25 | 0 | 0 | 65 | 65 | Absent | 17.9 |
| Example 27 | 10 | 24 | 16 | 0 | 40 | 0 | 0 | 50 | 50 | Absent | 27.6 |
| Example 28 | 10 | 30 | 20 | 0 | 50 | 0 | 0 | 40 | 40 | Absent | 32.8 |
| Comparative Example 46 | 10 | 36 | 24 | 0 | 60 | 0 | 0 | 30 | 30 | Absent | 38.2 |

| | Evaluation test | | | | | |
|---|---|---|---|---|---|---|
| | Dissolution properties | | Precipitation properties | | | |
| | Dissolution rate (% by mass) | Evaluation | Identification of precipitation | Oil phase dissolution rate (% by mass) | Evaluation | Overall evaluation |
| Example 23 | 68 | A | A | 102 | Good | AAA |
| Example 24 | 46 | A | A | 96 | Good | AAA |
| Example 25 | 40 | A | B | 83 | Good | B |
| Comparative Example 45 | 35 | A | C | 0 | Poor | D |
| Example 26 | 56 | A | A | 99 | Good | AAA |
| Example 27 | 36 | A | A | 99 | Good | AAA |
| Example 28 | 30 | A | B | 74 | Good | C |
| Comparative Example 46 | 26 | A | C | 40 | Poor | D |

TABLE 7

| | FLV | Aqueous solvent (% by mass) | | | | Nonaqueous carrier (% by mass) | | | | Evaluation test | |
|---|---|---|---|---|---|---|---|---|---|---|---|
| | | | | | | | | | | Presence or absence of turbidity | Dissolution properties |
| | (% by mass) | EtOH | PG | BnOH | Total amount | BnBz | Sesame oil | Castor oil | Total amount | | Solubility (% by mass) |
| Example 29 | 8 | 15 | 10 | 0 | 25 | 0 | 0 | 67 | 67 | Absent | 16.6 |
| Example 30 | 9 | 15 | 10 | 0 | 25 | 0 | 0 | 66 | 66 | Absent | 17.2 |
| Example 31 | 10.5 | 15 | 10 | 0 | 25 | 0 | 0 | 65 | 65 | Absent | 17.0 |
| Example 32 | 11 | 15 | 10 | 0 | 25 | 0 | 0 | 64 | 64 | Absent | 17.3 |
| Example 33 | 12 | 15 | 10 | 0 | 25 | 0 | 0 | 63 | 63 | Absent | 18.6 |
| Example 34 | 14 | 15 | 10 | 0 | 25 | 0 | 0 | 61 | 61 | Absent | 18.2 |
| Comparative Example 47 | 15 | 15 | 10 | 0 | 25 | 0 | 0 | 60 | 60 | Absent | NT |
| Comparative Example 48 | 16 | 15 | 10 | 0 | 25 | 0 | 0 | 59 | 59 | Absent | NT |
| Comparative Example 49 | 18 | 15 | 10 | 0 | 25 | 0 | 0 | 57 | 57 | Absent | NT |
| Comparative Example 50 | 20 | 15 | 10 | 0 | 25 | 0 | 0 | 55 | 55 | Absent | NT |
| Example 101 | 21 | 21 | 3 | 0 | 24 | 0 | 0 | 55 | 55 | Absent | 24.7 |
| Example 102 | 26 | 21 | 3 | 0 | 24 | 0 | 0 | 50 | 50 | Absent | 26.5 |
| Comparative Example 101 | 31 | 21 | 3 | 0 | 24 | 0 | 0 | 45 | 45 | Present | 28.4 |

| | Evaluation test | | | | | |
|---|---|---|---|---|---|---|
| | Dissolution properties | | Precipitation properties | | | |
| | Dissolution rate (% by mass) | Evaluation | Identification of precipitation | Oil phase dissolution rate (% by mass) | Evaluation | Overall evaluation |
| Example 29 | 48 | A | A | 99 | Good | AAA |
| Example 30 | 52 | A | A | 102 | Good | AAA |
| Example 31 | 62 | A | A | 103 | Good | AAA |
| Example 32 | 64 | A | A | 100 | Good | AAA |
| Example 33 | 64 | A | A | 99 | Good | AAA |
| Example 34 | 77 | B | B | 74 | Good | C |
| Comparative Example 47 | NT | — | C | 66 | Poor | D |
| Comparative Example 48 | NT | — | C | 23 | Poor | D |

TABLE 7-continued

|   | FLV | | | | | | | | |
|---|---|---|---|---|---|---|---|---|---|
| Comparative Example 49 | | | | | NT | — | C | 41 | Poor | D |
| Comparative Example 50 | | | | | NT | — | C | 29 | Poor | D |
| Example 101 | | | | | 85 | C | A | 91 | Good | A |
| Example 102 | | | | | 98 | D | A | 92 | Good | D |
| Comparative Example 101 | | | | | >100 | D | NT | NT | — | D |

TABLE 8

| | FLV (% by mass) | Aqueous solvent (% by mass) | | | | Nonaqueous carrier (% by mass) | | | | Evaluation test | |
|---|---|---|---|---|---|---|---|---|---|---|---|
| | | EtOH | PG | BnOH | Total amount | BnBz | Sesame oil | Castor oil | Total amount | Presence or absence of turbidity | Dissolution properties Solubility (% by mass) |
| Comparative Example 51 | 10 | 15 | 15 | 5 | 35 | 0 | 0 | 55 | 55 | Absent | 16.4 |
| Comparative Example 52 | 9.5 | 15 | 15 | 5 | 35 | 0 | 0 | 56 | 56 | Absent | NT |
| Comparative Example 53 | 9 | 15 | 15 | 5 | 35 | 0 | 0 | 56 | 56 | Absent | NT |
| Comparative Example 54 | 8 | 15 | 15 | 5 | 35 | 0 | 0 | 57 | 57 | Absent | NT |
| Comparative Example 55 | 10 | 8 | 15 | 12 | 35 | 0 | 0 | 55 | 55 | Absent | 11.3 |
| Comparative Example 56 | 10 | 9 | 15 | 11 | 35 | 0 | 0 | 55 | 55 | Absent | 12.3 |
| Comparative Example 57 | 10 | 10 | 15 | 10 | 35 | 0 | 0 | 55 | 55 | Absent | 12.4 |
| Comparative Example 58 | 10 | 11 | 15 | 9 | 35 | 0 | 0 | 55 | 55 | Absent | 13.3 |
| Comparative Example 59 | 10 | 12 | 15 | 8 | 35 | 0 | 0 | 55 | 55 | Absent | 14.0 |
| Comparative Example 60 | 10 | 15 | 15 | 5 | 35 | 0 | 0 | 55 | 55 | Absent | 16.5 |
| Comparative Example 61 | 10 | 10 | 13 | 12 | 35 | 0 | 0 | 55 | 55 | Absent | 12.3 |
| Comparative Example 62 | 10 | 11 | 13 | 11 | 35 | 0 | 0 | 55 | 55 | Absent | 13.0 |
| Comparative Example 63 | 10 | 12 | 13 | 10 | 35 | 0 | 0 | 55 | 55 | Absent | 13.4 |
| Comparative Example 64 | 10 | 15 | 10 | 10 | 35 | 0 | 0 | 55 | 55 | Absent | 15.5 |
| Comparative Example 65 | 10 | 13 | 10 | 13 | 35 | 0 | 0 | 55 | 55 | Absent | 13.2 |
| Comparative Example 66 | 10 | 10 | 10 | 15 | 35 | 0 | 0 | 55 | 55 | Absent | 12.4 |

| | Evaluation test | | | | | |
|---|---|---|---|---|---|---|
| | Dissolution properties | | Precipitation properties | | | |
| | Dissolution rate (% by mass) | Evaluation | Identification of precipitation | Oil phase dissolution rate (% by mass) | Evaluation | Overall evaluation |
| Comparative Example 51 | 61 | A | C | 25 | Poor | D |
| Comparative Example 52 | NT | — | C | 29 | Poor | D |
| Comparative Example 53 | NT | — | C | 31 | Poor | D |
| Comparative Example 54 | NT | — | C | 49 | Poor | D |
| Comparative Example 55 | 89 | C | C | 23 | Poor | D |
| Comparative Example 56 | 81 | C | C | 23 | Poor | D |
| Comparative Example 57 | 81 | C | C | 23 | Poor | D |

TABLE 8-continued

| | | | | | | |
|---|---|---|---|---|---|---|
| Comparative Example 58 | 75 | B | C | 23 | Poor | D |
| Comparative Example 59 | 71 | B | C | 23 | Poor | D |
| Comparative Example 60 | 61 | A | C | 25 | Poor | D |
| Comparative Example 61 | 81 | C | C | 22 | Poor | D |
| Comparative Example 62 | 77 | B | C | 22 | Poor | D |
| Comparative Example 63 | 75 | B | C | 23 | Poor | D |
| Comparative Example 64 | 65 | A | C | 23 | Poor | D |
| Comparative Example 65 | 76 | B | C | 22 | Poor | D |
| Comparative Example 66 | 81 | C | C | 22 | Poor | D |

TABLE 9

| | FLV (% by mass) | Aqueous solvent (% by mass) | | | | Nonaqueous carrier (% by mass) | | | | Evaluation test | |
|---|---|---|---|---|---|---|---|---|---|---|---|
| | | EtOH | PG | 1,3-BG | Total amount | BnBz | Peanut oil | Castor oil | Total amount | Presence or absence of turbidity | Dissolution properties Solubility (% by mass) |
| Example 35 | 10 | 15 | 0 | 10 | 25 | 0 | 0 | 65 | 65 | Absent | 17.2 |
| Example 36 | 10 | 15 | 10 | 0 | 25 | 0 | 5 | 60 | 65 | Absent | 16.9 |

| | Evaluation test | | | | | |
|---|---|---|---|---|---|---|
| | Dissolution properties | | Precipitation properties | | | |
| | Dissolution rate (% by mass) | Evaluation | Identification of precipitation | Oil phase dissolution rate (% by mass) | Evaluation | Overall evaluation |
| Example 35 | 58 | A | A | 100 | Good | AAA |
| Example 36 | 59 | A | A | 98 | Good | AAA |

TABLE 10

| | FLV (% by mass) | Aqueous solvent (% by mass) | | | Nonaqueous carrier (% by mass) | | | | Evaluation test | |
|---|---|---|---|---|---|---|---|---|---|---|
| | | EtOH | PG | Total amount | BnBz | Vegetable oil which is different from castor oil | | Castor oil | Total amount | Presence or absence of turbidity | Dissolution properties Solubility (% by mass) |
| Example 37 | 10 | 15 | 10 | 25 | 0 | Sesame oil | 1 | 64 | 65 | Absent | 19.8 |
| Example 38 | 10 | 15 | 10 | 25 | 0 | Sesame oil | 3 | 62 | 65 | Absent | 19.2 |
| Example 39 | 10 | 15 | 10 | 25 | 0 | Sesame oil | 6 | 59 | 65 | Absent | 19.3 |
| Example 40 | 10 | 15 | 10 | 25 | 0 | Soybean oil | 1 | 64 | 65 | Absent | 19.8 |
| Example 41 | 10 | 15 | 10 | 25 | 0 | Soynean oil | 3 | 62 | 65 | Absent | 19.5 |
| Example 42 | 10 | 15 | 10 | 25 | 0 | Soybean oil | 6 | 59 | 65 | Absent | 19.5 |
| Example 43 | 10 | 15 | 10 | 25 | 0 | Soybean oil | 10 | 55 | 65 | Absent | 18.9 |
| Example 44 | 10 | 15 | 10 | 25 | 0 | Camellia oil | 3 | 62 | 65 | Absent | 19.2 |
| Example 45 | 10 | 15 | 10 | 25 | 0 | Corn oil | 1 | 64 | 65 | Absent | 19.4 |
| Example 46 | 10 | 15 | 10 | 25 | 0 | Corn oil | 3 | 62 | 65 | Absent | 19.2 |
| Example 47 | 10 | 15 | 10 | 25 | 0 | Corn oil | 6 | 59 | 65 | Absent | 19.0 |
| Example 48 | 10 | 15 | 10 | 25 | 0 | Corn oil | 10 | 55 | 65 | Absent | 18.9 |
| Example 49 | 10 | 15 | 10 | 25 | 0 | Cottonseed oil | 3 | 62 | 65 | Absent | 19.5 |

TABLE 10-continued

| | | | | | | | | | | | |
|---|---|---|---|---|---|---|---|---|---|---|---|
| Example 50 | 10 | 15 | 10 | 25 | 0 | Medium-chain fatty acid triglyceride | 3 | 62 | 65 | Absent | 19.6 |
| Example 51 | 10 | 15 | 10 | 25 | 0 | Olive oil | 3 | 62 | 65 | Absent | 19.2 |
| Example 52 | 10 | 15 | 10 | 25 | 0 | Safflower oil | 3 | 62 | 65 | Absent | 19.0 |
| Example 53 | 10 | 15 | 10 | 25 | 0 | Rapeseed oil | 3 | 62 | 65 | Absent | 18.9 |

| | Evaluation test | | | | |
|---|---|---|---|---|---|
| | Dissolution properties | Precipitation properties | | | |
| | | Identification of precipitation | Oil phase | | |
| | Dissolution rate (% by mass) | Evaluation | | Oil phase dissolution rate (% by mass) | Evaluation | Overall evaluation |
| Example 37 | 51 | A | A | 98 | Good | AAA |
| Example 38 | 52 | A | A | 98 | Good | AAA |
| Example 39 | 52 | A | A | 98 | Good | AAA |
| Example 40 | 51 | A | A | 97 | Good | AAA |
| Example 41 | 51 | A | A | 97 | Good | AAA |
| Example 42 | 51 | A | A | 97 | Good | AAA |
| Example 43 | 53 | A | A | 99 | Good | AAA |
| Example 44 | 52 | A | A | 98 | Good | AAA |
| Example 45 | 52 | A | A | 98 | Good | AAA |
| Example 46 | 52 | A | A | 96 | Good | AAA |
| Example 47 | 53 | A | A | 99 | Good | AAA |
| Example 48 | 53 | A | A | 97 | Good | AAA |
| Example 49 | 51 | A | A | 98 | Good | AAA |
| Example 50 | 51 | A | A | 98 | Good | AAA |
| Example 51 | 52 | A | A | 100 | Good | AAA |
| Example 52 | 53 | A | A | 95 | Good | AAA |
| Example 53 | 53 | A | A | 98 | Good | AAA |

In Tables 1 to 10, "–" means that there is no available data.

In Tables 1 to 10, "NT" means that no test was conducted.

In Tables 1 to 10, "fulvestrant" was denoted as "FLV", "ethanol" as "EtOH", "propylene glycol" as "PG", "1,3-butylene glycol" as "1,3-BG", "benzyl alcohol" as "BnOH", and "benzyl benzoate" as "BnBz".

"Medium-chain fatty acid triglyceride" in Table 10 is a medium-chain fatty acid triglyceride (trade name: Myglyol (registered trademark) 812, constituent fatty acids: caprylic acid and capric acid), manufactured by Sasol.

The overall evaluation in Tables 1 to 10 was conducted according to evaluation standard as described in Table 11.

TABLE 11

| Overall evaluation | Presence or absence of turbidity | Dissolution rate | Oil phase dissolution rate |
|---|---|---|---|
| AAA | Absent | Equal to or less than 70% by mass | Equal to or greater than 90% by mass |
| AA | Absent | Greater than 70% by mass and equal to or less than 80% by mass | Equal to or greater than 90% by mass |
| A | Absent | Greater than 80% by mass and equal to or less than 90% by mass | Equal to or greater than 90% by mass |
| B | Absent | Equal to or less than 90% by mass | Equal to or greater than 80% by mass and less than 90% by mass |
| C | Absent | Equal to or less than 90% by mass | Equal to or greater than 70% by mass and less than 80% by mass |
| D | Absent | Equal to or less than 90% by mass | Less than 70% by mass |

TABLE 11-continued

| Overall evaluation | Presence or absence of turbidity | Dissolution rate | Oil phase dissolution rate |
|---|---|---|---|
| | Absent | Greater than 90% by mass | — |
| | Present | — | — |

As shown in Tables 1 to 10, in the pharmaceutical compositions of Examples 1 to 53, 101, and 102, precipitation of fulvestrant became difficult to occur even in a case where each pharmaceutical composition was added dropwise to a physiological saline solution. In addition, in the pharmaceutical compositions of Examples 1 to 53, 101, and 102, good dissolution properties of fulvestrant were exhibited, phase separation or precipitation became difficult to occur in ingredients contained in the pharmaceutical composition even in a case of being stored at a low temperature, and a state in which ingredients such as fulvestrant are well mixed was stably retained.

From these results, it was found that the pharmaceutical compositions of Examples 1 to 53, 101, and 102 are pharmaceutical preparations suitable for intramuscular injection in view of the fact that precipitation of fulvestrant becomes difficult to occur in a case of being brought into contact with a body fluid while fulvestrant is contained at a concentration of equal to or greater than 8% by mass, which is higher than the related art (5% by mass), with respect to the entire mass of the pharmaceutical composition.

On the other hand, in the pharmaceutical compositions of Comparative Examples 1 to 66 and 101, in a case where fulvestrant is contained at a concentration of equal to or greater than 8% by mass, which is high as compared with the related art, with respect to the entire mass of the pharmaceutical composition, good results were not obtained in at least one evaluation among evaluation for presence or absence of turbidity, evaluation for dissolution properties of fulvestrant, or evaluation for precipitation properties.

Disclosures of Japan Patent Application No. 2016-076759 filed on Apr. 6, 2016, Japanese Patent Application No. 2016-203705 filed on Oct. 17, 2016, and Japanese Patent Application No. 2017-063914 filed on Mar. 28, 2017 are hereby incorporated by reference in their entirety.

All publications, patent applications, and technical standards described in the present specification are herein incorporated by reference to the same extent as a case where each individual publication, patent application, or technical standard was specifically and individually indicated to be incorporated by reference.

What is claimed is:

1. A pharmaceutical composition comprising:
fulvestrant;
an aqueous solvent, which is a solvent having a high compatibility with water; and
a pharmaceutically acceptable nonaqueous carrier, the nonaqueous carrier being a liquid substance having a solubility in water at 25° C. of less than 1% by mass;
wherein the pharmaceutical composition does not contain benzyl alcohol; and
wherein a content of the fulvestrant is 8% by mass to 14% by mass with respect to the entire mass of the pharmaceutical composition, the aqueous solvent satisfies the following requirements (1) to (3), and the pharmaceutically acceptable nonaqueous carrier satisfies the following requirements (A) and (B):
(1) ethanol is contained in an amount of 8% by mass to 30% by mass with respect to the entire mass of the pharmaceutical composition;
(2) propylene glycol is contained in an amount of 10% by mass to 20% by mass with respect to the entire mass of the pharmaceutical composition;
(3) a content of the aqueous solvent is 20% by mass to 50% by mass with respect to the entire mass of the pharmaceutical composition;
(A) a content of benzyl benzoate is less than 1% by mass with respect to the entire mass of the pharmaceutical composition;
(B) a content of the pharmaceutically acceptable nonaqueous carrier is 40% by mass to 70% by mass with respect to the entire mass of the pharmaceutical composition.

2. The pharmaceutical composition according to claim 1, wherein the pharmaceutically acceptable nonaqueous carrier is castor oil, or a mixture of castor oil and vegetable oil which is different from castor oil.

3. The pharmaceutical composition according to claim 2, wherein the vegetable oil which is different from castor oil is at least one kind of vegetable oil selected from the group consisting of sesame oil, peanut oil, soybean oil, *camellia* oil, corn oil, cottonseed oil, olive oil, safflower oil, rapeseed oil, and a fatty acid triglyceride of which constituent fatty acids have 6 to 12 carbon atoms on average.

4. The pharmaceutical composition according to claim 2, wherein the vegetable oil which is different from castor oil is at least one kind of vegetable oil selected from sesame oil or peanut oil.

5. The pharmaceutical composition according to claim 1, wherein the pharmaceutically acceptable nonaqueous carrier further satisfies the following requirements (C) and (D):
(C) castor oil is contained in an amount of 40% by mass to 70% by mass with respect to the entire mass of the pharmaceutical composition;
(D) a content of the vegetable oil which is different from castor oil is less than 20% by mass with respect to the entire mass of the pharmaceutical composition.

6. The pharmaceutical composition according to claim 1, wherein a content of ethanol is 10% by mass to 20% by mass with respect to the entire mass of the pharmaceutical composition.

7. A pharmaceutical composition comprising:
fulvestrant;
an aqueous solvent, which is a solvent having a high compatibility with water; and
a pharmaceutically acceptable nonaqueous carrier, the nonaqueous carrier being a liquid substance having a solubility in water at 25° C. of less than 1% by mass;
wherein the pharmaceutical composition does not contain benzyl alcohol; and
wherein a content of the fulvestrant is 8% by mass to 14% by mass with respect to the entire mass of the pharmaceutical composition, the aqueous solvent satisfies the following requirements (i) to (iii), and the pharmaceutically acceptable nonaqueous carrier satisfies the following requirements (a) to (d):
(i) ethanol is contained in an amount of 10% by mass to 20% by mass with respect to the entire mass of the pharmaceutical composition;
(ii) propylene glycol is contained in an amount of 10% by mass to 20% by mass with respect to the entire mass of the pharmaceutical composition;
(iii) a content of the aqueous solvent is 20% by mass to 40% by mass with respect to the entire mass of the pharmaceutical composition;
(a) a content of benzyl benzoate is less than 1% by mass with respect to the entire mass of the pharmaceutical composition;
(b) castor oil is contained in an amount of 40% by mass to 70% by mass with respect to the entire mass of the pharmaceutical composition;
(c) a content of at least one kind of vegetable oil selected from sesame oil or peanut oil is less than 20% by mass with respect to the entire mass of the pharmaceutical composition;
(d) a content of the pharmaceutically acceptable nonaqueous carrier is 40% by mass to 70% by mass with respect to the entire mass of the pharmaceutical composition.

8. The pharmaceutical composition according to claim 1, which is for intramuscular injection.

9. The pharmaceutical composition according to claim 7, which is for intramuscular injection.

* * * * *